US007457753B2

(12) United States Patent
Moran et al.

(10) Patent No.: US 7,457,753 B2
(45) Date of Patent: Nov. 25, 2008

(54) TELEPHONE PATHOLOGY ASSESSMENT

(75) Inventors: Rosalyn Moran, Blackrock (IE); Richard Reilly, Ballsbridge (IE); Philip De Chazal, Monkstown (IE); Brian O'Mullane, Rathfarnham (IE); Peter Lacy, Howth (IE)

(73) Assignee: University College Dublin National University of Ireland, Dublin (IE)

( * ) Notice: Subject to any disclaimer, the term of this patent is extended or adjusted under 35 U.S.C. 154(b) by 630 days.

(21) Appl. No.: 11/168,312

(22) Filed: Jun. 29, 2005

(65) Prior Publication Data

US 2007/0005357 A1 Jan. 4, 2007

(51) Int. Cl.

| | |
|---|---|
| ***A61B 5/08*** | (2006.01) |
| ***G06F 3/048*** | (2006.01) |
| ***G10L 11/04*** | (2006.01) |
| ***G10L 15/00*** | (2006.01) |
| ***G10L 17/00*** | (2006.01) |
| ***G10L 21/00*** | (2006.01) |

(52) U.S. Cl. ....................... 704/270; 600/529; 600/538; 704/206; 704/246; 704/250; 704/E17.002; 715/767

(58) Field of Classification Search ................. 704/270; 600/529, 238

See application file for complete search history.

(56) References Cited

U.S. PATENT DOCUMENTS

| | | | | |
|---|---|---|---|---|
| 6,519,562 | B1 * | 2/2003 | Phillips et al. | 704/240 |
| 7,127,400 | B2 * | 10/2006 | Koch | 704/270.1 |
| 2002/0135618 | A1 * | 9/2002 | Maes et al. | 345/767 |
| 2003/0036903 | A1 * | 2/2003 | Konopka et al. | 704/249 |
| 2003/0069728 | A1 * | 4/2003 | Tato et al. | 704/231 |
| 2004/0006474 | A1 * | 1/2004 | Gong et al. | 704/270.1 |
| 2005/0102135 | A1 * | 5/2005 | Goronzy et al. | 704/213 |
| 2005/0246168 | A1 * | 11/2005 | Campbell et al. | 704/214 |
| 2005/0267739 | A1 * | 12/2005 | Kontio et al. | 704/205 |
| 2006/0085189 | A1 * | 4/2006 | Dalrymple et al. | 704/250 |

OTHER PUBLICATIONS

Ludlow et al., 'Application of pitch perturbation measures to the assessment of hoarseness in Parkinson's disease', The Journal of the Acoustical Society of America—Nov. 1979—vol. 66, Issue S1, pp. S64-S65.*

* cited by examiner

*Primary Examiner*—David R Hudspeth
*Assistant Examiner*—Justin W Rider
(74) *Attorney, Agent, or Firm*—Nath Law Group; Jerald L. Meyer; Sung Y. Chung

(57) ABSTRACT

A system for remote assessment of a user is disclosed. The system comprises application software resident on a server and arranged to interact across a network with a user operating a client device to obtain one or more sample signals of the user's speech. A datastore is arranged to store the user speech samples in association with details of the user. A feature extraction engine is arranged to extract one or more first features from respective speech samples. A comparator is arranged to compare the first features extracted from a speech sample with second features extracted from one or more reference samples and to provide a measure of any differences between the first and second features for assessment of the user.

20 Claims, 1 Drawing Sheet

TELEPHONE PATHOLOGY ASSESSMENT

FIELD OF THE INVENTION

The present invention relates to a method and system for remote assessment of a user.

BACKGROUND OF THE INVENTION

C. Maguire, P. de Chazal, R. B. Reilly, P. Lacy "Automatic Classification of voice pathology using speech analysis", World Congress on Biomedical Engineering and Medical Physics, Sydney, August 2003; and C. Maguire, P. de Chazal, R. B. Reilly, P. Lacy "Identification of Voice Pathology using Automated Speech Analysis", Proc. of the 3rd International Workshop on Models and Analysis of Vocal Emission for Biomedical Applications, Florence, December 2003 disclose methods to aid in early detection, diagnosis, assessment and treatment of laryngeal disorders including feature extraction from acoustic signals to aid diagnosis.

J. I. Godino-Llorente, P Gomez-Vilda, "Automatic Detection of Voice Impairments by means of Short-Term Cepstral Parameters and Neural Network Based Detectors" *IEEE Transactions on Biomedical Engineering* Vol. 51, No. 2, pp. 380-384, February 2004 discloses a neural network based detector that is based on short-term cepstral parameters for discrimination between normal and abnormal speech samples. Using a subset of 135 voices from a publicly available database, Mel frequency cepstral coefficients (MFCCs) and their derivatives were employed as input features to a classifier which achieved an accuracy of 96.0% in classifying normal and abnormal voices.

Common to these and other prior art pathology detection systems is the recording environments of the voice samples under test. These comprise controlled recordings (soundproof recording room, set distance from patient to microphone) recorded at a sampling rate of approximately 25 kHz.

DISCLOSURE OF THE INVENTION

According to the present invention there is provided a system for remote assessment of a user according to claim 1.

BRIEF DESCRIPTION OF THE DRAWINGS

Embodiments of the invention will now be described by way of example, with reference to the accompanying drawings, in which.

DESCRIPTION OF THE PREFERRED EMBODIMENTS

Figure 1:
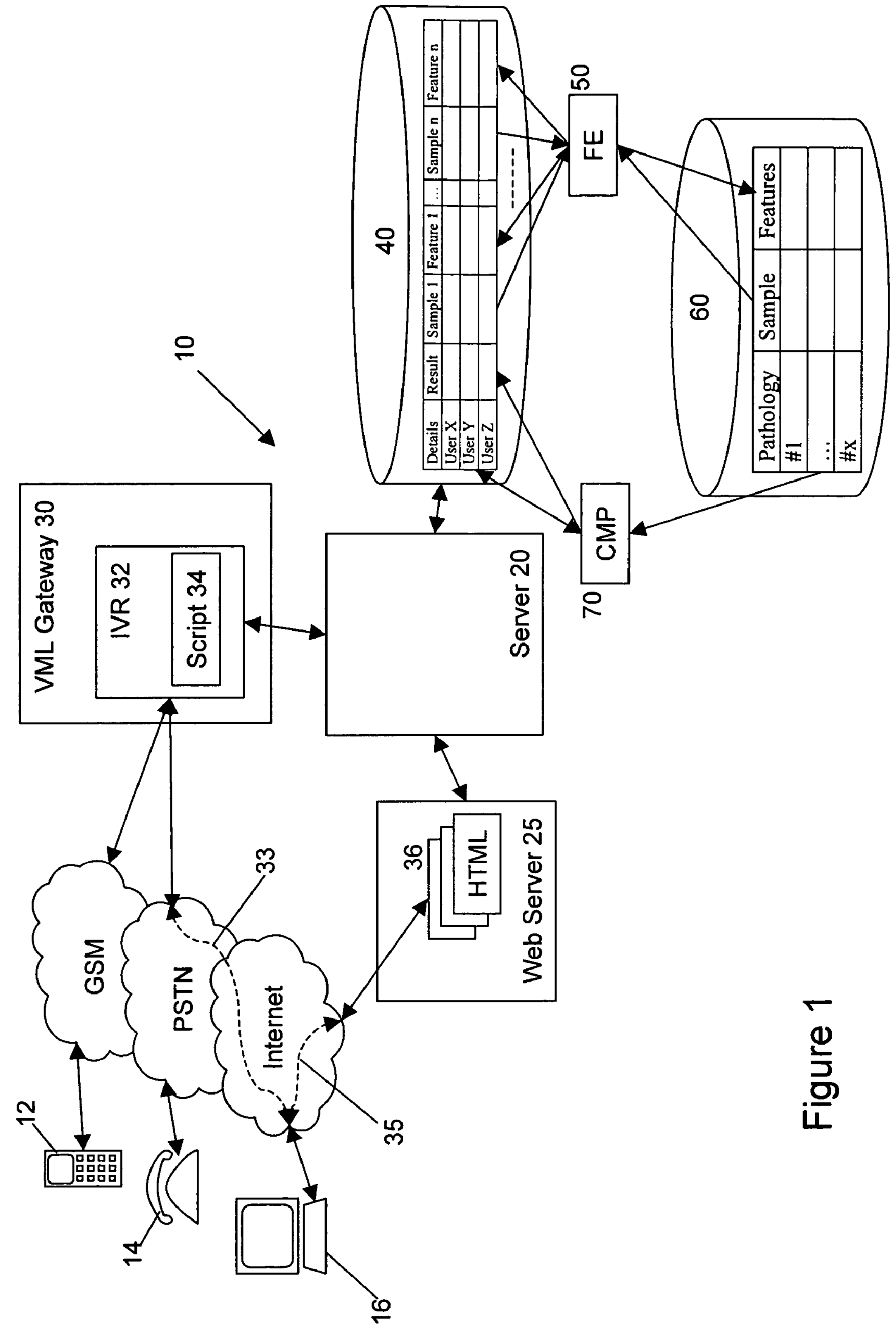
FIG. 1 is a schematic diagram of a system for remote assessment of a user according to a first embodiment of the invention.

Referring now to FIG. 1, in a first embodiment of the present invention, there is provided a system 10 of remotely detecting vocal fold pathologies using telephone quality speech. The system comprises a server 20 to which a remote user can connect using any one of a variety of client devices 12, 14, 16 equipped with a sound sampling mechanism.

One such device is a cellular/mobile phone 12 which connects across the GSM (Global System for Mobile Communications) network to the server 20 via a Voice XML gateway 30 running an Interactive Voice Recognition (IVR) application

32. Alternatively, a user can employ a conventional telephone 14 connecting across the PSTN (Public Switched Telephone Network) to the gateway 30.

The operation of the application 32 is governed by a script 34 which can be defined by an authoring package such as Voxbuilder produced by Voxpilot Limited, Dublin (www.voxpilot.com) and uploaded to the gateway 30 or uploaded to server 20 and linked back to gateway 30. The user through interaction with the application 32 in a conventional manner using any combination of tone and/or speech recognition provides their details and any authentication information required. During execution, the application 32 captures a speech sample and this along with the user details is transmitted to the server 20. In the preferred embodiment, the speech sample comprises a user's sustained phonation of the vowel sound /a/ (as in the English word "cap").

An alternative interface can be provided by the server 20 by way of a web application. Where a client computer 16 includes a microphone, again through interaction with the application comprising web pages 36 resident on a server 25 (as indicated by the line 35), the users details as well as a speech sample can be captured and transmitted to the server 20.

It will also be seen that a networked client computing device 16 can also be used to make, for example, an Internet telephony session connection with the IVR application 32 (as indicated by the line 33) in a manner analogous to the clients 12, 14.

User details and their associated speech sample(s) are stored by the server 20 in a database 40. The speech sample can be stored in any suitable for including in PCM (Pulse Code Modulation) or the sample may be stored in a coded form such as MP3 so that certain features such as harmonic or noise values can more easily be extracted from the signal at a later time.

According to requirements, either immediately in response to a speech samples being added to the database 40 or offline in batch mode, a feature extraction (FE) engine 50, processes each speech sample to extract its associated features which will be discussed in more detail later.

As well as the database 40, in the first embodiment, a database 60 of x=631 speech samples of the sustained phonation of the vowel sound /a/ is derived from the Disordered Voice Database Model 4337 acquired at the Massachusetts Eye and Ear Infirmary (MEEI) Voice and Speech Laboratory and distributed by Kay Elemetrics (4337 database) originally recorded at a sampling rate of 25 kHz.

The mixed gender 4337 database contains 631 voice recordings, each with an associated clinical diagnosis—573 from patients exhibiting a pathology and 58 for normal patients. The types of pathologies are diverse, ranging from Vocal Fold Paralysis to Vocal Fold Carcinoma. Vocalisations last from 1-3 seconds, over which time, periodicity should remain constant.

In the preferred embodiment, classification based on such steady state phonations is preferred to sentence based normal/abnormal classification. Within steady state phonations, it has been shown that the phoneme /a/ outperforms the higher cord-tension /i/ and /e/ phonemes.

In the first embodiment, speech samples from the database 4337 database were played over a long distance telephone channel to provide the speech samples stored in the database 60. This process created a telephone quality voice pathology database for all 631 voice recordings in the 4337 database.

As an equivalent to being transmitted over actual phone lines, the speech samples of the 4337 database could be downsampled to limit bandwidth followed by a linear filter modelling the channel characteristics of the analogue first-hop in a telephone circuit followed then by an additive noise source, as illustrated in Table 1.

TABLE 1

| Pre-processing of voice sample database | | | |
|---|---|---|---|
| 1. | 2. | 3. | 4. |
| Pre-distortion, 10 kHz. | Downsample to 8 kHz: Effective bandwidth 4 kHz. | Spectral Shaping: Linear filter 200 Hz-3400 Hz. | Add noise: Additive white gaussian noise at 30 dB SNR |

Nonetheless, it will be seen that that if high quality samples were available these could be stored in the database 60 and used in their high quality form.

As in the case of the samples in the database 40, the feature extraction engine processes each of the speech samples in the database 60 to provide their respective feature vectors.

In the preferred embodiment, in general, the features extracted comprise pitch perturbation features, amplitude perturbation features and a set of measures of the harmonic-to-noise ratio (HNR). Preferably, the features extracted include the fundamental frequency (F0), jitter (short-term, cycle to cycle, perturbation in the fundamental frequency of the voice), shimmer (short-term, cycle to cycle, perturbation in the amplitude of the voice), signal-to-noise ratios and harmonic-to-noise ratios.

Referring to Tables 2 and 3, pitch and amplitude perturbation measures were calculated by segmenting the speech waveform (2-5 seconds in length) into overlapping 'epochs'. Each epoch is 20 msecond in duration with an overlap of 75% between successive epochs. For each epoch i, the value of the fundamental frequency, or pitch $F_i$, is calculated and returned with its corresponding amplitude measure $A_i$. These epoch values are used to create two one-dimensional vectors, defining that particular voice recordings' "pitch contour" (the fundamental frequency captured over time) and "amplitude contour". $N_{voice}$ is a counting measure of any difference in pitch/amplitude between epoch value i and epoch value i+1 and n is the number of epochs extracted.

Mel Frequency Cepstral Coefficients (MFCC) features are commonly used in Automatic Speech Recognition (ASR) and also Automatic Speaker Recognition systems. The Cepstral domain is employed in speech processing, as the lower valued cepstral "quefrencies" model the vocal tract spectral dynamics, while the higher valued quefrencies contain pitch information, seen as equidistant peaks in the spectra.

The Harmonic to Noise Ratio measures for a speech sample is calculated in the Cepstral domain, as follows:

1. Initially, the time domain signal, e.g. PCM format, for the speech sample is normalised to have zero mean and unit variance. This comprises calculating the mean and standard deviation for the individual samples of the speech sample. The mean amplitude value is then subtracted from each original sample value giving positive and negative valued samples with mean equal to zero. Each of these values is then subsequently divided by the standard deviation, producing sample values with variance equal to one.
2. In the preferred embodiment, the normalised samples for a 100 msecond epoch, are extracted from the middle of the speech sample.
3. The samples for the epoch are transformed into the frequency domain and a peak-picking algorithm locates the peaks at multiples of the fundamental frequency.
4. A bandstop filter in the Cepstral domain is applied to the signal. The stopband of the filter is limited to the width of each peak. The remaining signal is known as the rahmonics (harmonics in the cepstral domain) comb-liftered signal and contains the noise information.
5. The Fourier transform of this comb-liftered signal is taken, generating an estimate of the noise energy present N(f). Similarly, the Fourier Transform of the original cepstral-domain signal, including rahmonics is taken, O(f).
6. The HNR for a given frequency band B is then calculated as per $$HNR_{\beta}(f)=\text{mean}(O(f))_{\beta}-\text{mean}(N(f))_{\beta}$$

Eleven HNR measures were calculated, as illustrated in Table 4.

TABLE 2

| Pitch Perturbation features | | |
|---|---|---|
| No | Description | Calculation Method |
| 1 | Mean F0 (F0_av) | $\frac{1}{n}\sum_{i=1}^{n} F_i$ |
| 2 | Maximum F0 Detected (F0_hi) | max ($F_i$) |
| 3 | Minimum F0 Detected (F0_lo) | min ($F_i$) |
| 4 | Standard Deviation of F0 contour | $\frac{1}{n-1}\sum_{i=1}^{n}(F_i-\bar{F})^2$ |
| 5 | Phonatory Frequency Range | $12\times\frac{\log\left(\frac{F0\_hi}{F0\_lo}\right)}{\log 2}$ |
| 6 | Mean Absolute Jitter (MAJ) | $\frac{1}{n-1}\sum_{i=n-1}^{1}\lvert F_{i+1}-F_i\rvert$ |

TABLE 2-continued

Pitch Perturbation features

| No | Description | Calculation Method |
|---|---|---|
| 7 | Jitter (%) | $\frac{MAJ}{F0\_av}$ |
| 8 | Relative Average Perturbation smoothed over 3 pitch periods | $\frac{\frac{1}{n-2}\sum_{i=2}^{n-1}\left\|\frac{F_{i+1}+F_i+F_{i-1}}{3}-F_i\right\|}{F0\_av}\times 100$ |
| 9 | Pitch Perturbation Quotient smoothed over 5 pitch periods | $\frac{\frac{1}{n-4}\sum_{i=3}^{n-2}\left\|\frac{\sum_{k=i-2}^{i+2}F(k)}{5}-F_i\right\|}{F0\_av}\times 100$ |
| 10 | Pitch Perturbation Quotient smoothed over 55 pitch periods | $\frac{\frac{1}{n-54}\sum_{i=28}^{n-27}\left\|\frac{\sum_{k=i-27}^{i+27}F(k)}{55}-F_i\right\|}{F0\_av}\times 100$ |
| 11 | Pitch Perturbation Factor | $\frac{N_{p\geq threshold}}{N_{voice}}\times 100$ where, $*N_p$: epoch perturbation across time greater than 0.5 msec in magnitude |
| 12 | Directional Perturbation Factor | $\frac{N_{\Delta\pm}}{N_{voice}}\times 100$ where, $*N_{\Delta\pm}$: epoch perturbation across time for which there is a change in algebraic sign. |

TABLE 3

Amplitude Perturbation features

| No | Description | Calculation method |
|---|---|---|
| 1 | Mean Amp (Amp__av) | $\frac{1}{n}\sum_{i=1}^{n}A_i$ |
| 2 | Maximum Amp Detected | max $(A_i)$ |
| 3 | Minimum Amp Detected | min $(A_i)$ |
| 4 | Standard Deviation of Amp contour | $\frac{1}{n-1}\sum_{i=n-1}^{1}(A_i-\overline{A})^2$ |
| 5 | Mean Absolute Shimmer (MAS) | $\frac{1}{n-1}\sum_{i=n-1}^{1}\|A_{i+1}=A_i\|$ |
| 6 | Shimmer (%) | $\frac{MAS}{Amp\_av}$ |
| 7 | Shimmer: Decibels | $\frac{1}{n-1}\sum_{i=1}^{n-1}20\times\log\left(\frac{A_i}{A_{i+1}}\right)$ |

TABLE 3-continued

Amplitude Perturbation features

| No | Description | Calculation method |
|---|---|---|
| 8 | Amplitude Relative Average Perturbation smoothed over 3 pitch periods | $\dfrac{\frac{1}{n-2}\sum_{i=2}^{n-1}\left\lvert\frac{A_{i+1}+A_i+A_{i-1}}{3}-A_i\right\rvert}{Amp\_av}\times 100$ |
| 9 | Amplitude Perturbation Quotient smoothed over 5 pitch periods | $\dfrac{\frac{1}{n-4}\sum_{i=3}^{n-2}\left\lvert\frac{\sum_{k=i-2}^{i+2}A(k)}{5}-A_i\right\rvert}{Amp\_av}\times 100$ |
| 10 | Amplitude Perturbation Quotient smoothed over 55 pitch periods | $\dfrac{\frac{1}{n-54}\sum_{i=28}^{n-27}\left\lvert\frac{\sum_{k=i-27}^{i+27}A(k)}{55}-A_i\right\rvert}{Amp\_av}\times 100$ |
| 11 | Amplitude Perturbation Factor | $\dfrac{N_{p\geq threshold}}{N_{voice}}\times 100$ |
| 12 | Amplitude Directional Perturbation Factor | $\dfrac{N_{\Delta\pm}}{N_{voice}}\times 100$ |

TABLE 4

Harmonic to Noise Ratio Bands

| Band Number | Incorporating Frequencies (Hz) |
|---|---|
| 1 | 0-500 |
| 2 | 0-1000 |
| 3 | 0-2000 |
| 4 | 0-3000 |
| 5 | 0-4000 |
| 6 | 0-5000 |
| 7 | 500-1000 |
| 8 | 1000-2000 |
| 9 | 2000-3000 |
| 10 | 3000-4000 |
| 11 | 4000-5000 |

Again, according to requirements, in a first embodiment of the invention, a classification engine 70 is arranged to compare feature vectors for respective speech samples (probes) provided by remote users of the client devices 12, 14 or 16 to feature vectors from the database 60 either as they are written to the database or offline in batch mode.

In the first embodiment, the feature vectors of the database 60 are used to test and train automatic classifiers employing Linear Discriminant Analysis. Then depending on the Euclidian distance from the probe to the various samples or clusters of samples of the database 60, an assessment of the user's condition may be made by the classification engine 70. It will be seen that the classification engine could be re-defined to use Hidden Markov Models which would utilise features extracted in the time domain and discriminate between pathological and normal using a non-linear network. This result can in turn be written to the database 40 where it can be made available to either a user and/or their clinician either through via server 20 through the applications 32, 36 or by any other means.

It will be seen that while the servers 20, 25 and 30 are shown in FIG. 1 as separate, these may in fact be combined as required. Also while the feature extraction engine 50 and classification engine 70 have been shown running independently, these could be implemented within any one or more of the servers 20, 25 and 30.

While a sustained phonation, recorded in a controlled environment, can be classified as normal or pathologic with accuracy greater than 90%, results for the first embodiment indicate that a telephone quality speech can be classified as normal or pathologic with an accuracy of 74.2%. It has been found that amplitude perturbation features prove most robust in channel transmission.

When the database 60 was subcategorised into four independent clusters/classes of samples, comprising normal, neuromuscular pathologic, physical pathologic and mixed (neuromuscular with physical) pathologic, it was found that using these homogenous training and testing clusters/sets improved classifier performance, with neuromuscular disorders being those most often correctly detected. Results show that neuromuscular disorders could be detected remotely with an accuracy of 87%, while physical abnormalities gave accuracies of 78% and mixed pathology voice were separated from normal voice with an accuracy of 61%.

In a second embodiment of the invention, there is provided a system for remotely recording the symptoms of asthma sufferers. In general the system comprises the same blocks as in FIG. 1 except that the database 60 is in general not required.

The second embodiment is distinct from the system of the first embodiment, where one speech sample need only be taken from a user for comparison against the database 60 to provide an assessment, in that multiple samples are taken for each user. The feature vectors for these samples are compared against the feature vectors for other speech samples from the same user to provide a record and an assessment of the user's condition over time.

So, for example, on or after registering for the system either through interaction with a modified IVR application 32 or web application 36, the user provides a speech sample when not exhibiting asthmatic symptoms. This is stored in the database 40 as a reference sample #1 along with its extracted feature vector. Subsequently, when a user begins to exhibit asthma symptoms or in order to assess the degree to which they exhibit asthma symptoms, they connect to the server 20 through any one of the clients 12-16 using the modified applications 32,36 and provide a further speech sample. This subsequently provided speech sample is recorded and its corresponding feature vector extracted by the FE engine 50. The distance of subsequently extracted feature vectors from the reference sample feature vector can be used as a measure of the degree of severity of the asthma attack. This measure can be normalised with reference to measures from the single user or with reference to measures taken from other users. Measures for users can in turn be used to assist a clinician in altering a patient's medication or in simply gaining an objective measure of the degree of severity of an attack, especially when the patient may only be in a position to report the attack to the clinician afterwards.

While the details provided above should be sufficient to enable the second embodiment to be implemented, it is worth noting that there has been some literature in the area of assessing spectro-temporal aspects of speech samples for asthma sufferers. These include:

Gavriely, Breath Sounds Methodology. CRC Press, 1995.

R A Sovijarvi, F Dalmasso, J Vanderschoot, Malmberg. Definition of terms for applications of respiratory sounds. Eur Respir Rev, 10:77, pp 597-610, 2000.

Hans Pasterkamp, Steve S Kraman and George Wodicka. Respiratory Sounds: Advances Beyond the Stethoscope. Am J Respir Crit Care Med. Vol 156. pp 974-987, 1997.

R. P Baughman and Loudon. Lung Sound analysis for continuous evaluation of airflow obstruction in asthma. Chest, Vol 88, 364-368, 1985

Meslier, N. G. Charbonneau, and J. L. Racineux. Wheezes. Eur. Respir J. 8 :1942-1948, 1995

Y Shabtai-Musih, J B Grotberg, N Gavriely. Spectral Content of Forced Expiratory Wheezes during air, He, and SF6 Breathing in Normal Humans. J Appl Physiol, 72:629-635, 1992.

Homs-Corbera, A., J. A. Fiz, J. Morera, R. Jané (2004). Time-Frequency Detection and Analysis of Wheezes during Forced Exhalation. IEEE Transactions on Biomedical Engineering, vol. 51, n. 1, pp. 182-186.

José A Fiz, Raimon Jané, D Salvatella, José Izquierdo, L Lores, P Caminal, Jose Morera. Analysis of traqueal sounds during forced exhalation in asthma patients and normal subject. Chest, 116, 3, 1999.

José A Fiz, Raimon Jané, Antoni Hons, José Izquierdo, Maria A Garcia and Jose Morera. Detection of wheezing during maximal forced exhalation in patients with obstructed airways. Chest, 122, pp: 186 191. 2002.

R. Jané, J. A Fiz, J. Morera. Analysis of Wheezes in Asthmatic Patients during Spontaneous Respiration. Proc of the 26$^{th}$ Annual International Conference of the IEEE EMBS pp. 3836-3839. 2004.

All have considered frequency analysis in the 100-2000 Hz range and these support the merit of results provided by a telephony based assessment application according to the second embodiment. As such, in a particularly preferred implementation of the second embodiment, sample audio signals can be acquired with a sampling frequency of as low as 5000 Hz. Each sample audio signal is preferably between 20 and 120 seconds long and includes at least one respiratory cycle. These samples are stored in the database 40 and each sample is associated both with the patient and also with details of the patient's state when providing the sample.

The FE engine 50 is adapted to first use a zero-crossing detector when processing stored or acquired sample audio signals. This involves analysing the audio signal in the time domain to separate stored or acquired sample audio signals into portions, each comprising an inspiration or an expiration phase of breathing. As in the case of HNR above, the individual samples of the audio signal are first normalised to have zero mean so giving individual positive and negative sample values. The zero-crossing detector parses the audio signal to determine where the sample values change sign. Contiguous groups of normalised samples valued above or below the mean are taken to indicate the mid point of an inpiration or expiratory phase. Alternate, contiguous groups of such signal samples are therefore taken as inpiration and expiratory phases respectively.

A signal portion comprising an expiratory phase is required to analyse respiratory sounds in spontaneous and forced manoeuvres, as it is known that there is a higher contribution of wheezing during expiration.

The FE engine 50 continues by analysing expiration phases for each respiratory cycle in the frequency domain as follows:

Each expiration phase sample signal portion is divided into segments (typically 14).

The power spectral density (PSD) of these segments is estimated, using an autoregressive model (typically of order 16). Preferably, only the central temporal segments are considered because the airflow is more stable in these segments. So for example, a central 10 segments can be chosen from 14 sample segments.

The mean frequency (F0 as discussed previously) or alternatively the peak frequency (used as F0) is estimated in the band 100-2000 Hz for each segment.

A mean or median value of F0 (feature 1 listed in Table 2) is obtained for the segments of a respiratory cycle.

A mean or median value of F0 can then be taken across all of the cycles of a sample signal.

The FE engine stores F0 for each speech sample produced by a patient in the database 40. Values of F0 can be studied for samples taken during different manoeuvres (spontaneous and forced) and patient state (baseline and after bronchodilator inhalation) and the patient can be guided through interaction with the application 32,36 to either conduct specific manoeuvres while providing their speech sample(s) or to supply details of their state when providing their speech sample(s).

It has been shown that analysis in the bandwidth 600-2000 Hz allows quantification of wheezes episodes. As such, if the F0 inside of the 600-2000 Hz band changes during a number of consecutive segments of a cycle, a wheeze is considered to have occurred in this expiration. The degree of fluctuation can used to assess the degree of obstruction in a patient's breathing and to follow-up with treatment or to adjust the treatment of the patient.

The invention claimed is:

1. A system for remote assessment of a user comprising:

application software resident on a server and arranged to interact across a network with a user operating a client device to obtain one or more sample signals of the user's speech;

a datastore arranged to store said one or more user speech samples in association with details of the user;

a feature extraction engine arranged to: extract one or more first features from respective speech samples; extract one or more second features from one or more reference samples, said reference samples comprising a database of speech samples, each sample having a pathology associated therewith, said pathologies comprising: normal, neuromuscular pathologic, physical pathologic and mixed pathologic; and store said second features in association with respective pathologies; and a comparator arranged to compare said first features extracted from a speech sample with second features extracted from said reference samples and to provide a measure of any differences between said first and second features for assessment of said user.

2. A system as claimed in claim 1 wherein said client is a cellular phone, said network includes the Global System for Mobile Communications (GSM) network, wherein said application software comprises an interactive voice recognition (IVR) application and wherein said server includes a voice mark-up language (VML) gateway.

3. A system as claimed in claim 1 wherein said client is a telephone handset, said network includes the public switched telephone network (PSTN), wherein said application software comprises an interactive voice recognition (IVR) application and wherein said server includes a voice mark-up language (VML) gateway.

4. A system as claimed in claim 1 wherein said client is a computing device, said network includes a packet switched network, wherein said application software comprises one or more web pages and wherein said server includes a web server.

5. A system as claimed in claim 1 wherein said first and second features comprise one or more of pitch perturbation, amplitude perturbation and harmonic-to-noise ratio features.

6. A system as claimed in claim 5 wherein said pitch perturbation features include a mean frequency measure for a sample signal.

7. A system for remote assessment of a user comprising:

application software resident on a server and arranged to interact across a network with a user operating a client device to obtain one or more sample signals of the user's speech, said sample signals comprising a sustained phonation of the vowel sound /a/;

a datastore arranged to store said one or more user speech samples in association with details of the user;

a feature extraction engine arranged to: extract one or more first features from respective speech samples; extract one or more second features from one or more reference samples, said reference samples comprising a database of speech samples, each sample having a pathology associated therewith; and store said second features in association with respective pathologies; and a comparator arranged to compare said first features extracted from a speech sample with second features extracted from said reference samples and to provide a measure of any differences between said first and second features for assessment of said user.

8. A system as claimed in claim 7 wherein said sample signals are between 2 and 5 seconds in length.

9. A system for remote assessment of a user comprising:

application software resident on a server and arranged to interact across a network with a user operating a client device to obtain one or more sample signals of the user's speech;

a datastore arranged to store said one or more user speech samples in association with details of the user;

a feature extraction engine arranged to extract one or more first features from respective speech samples; and a comparator arranged to compare said first features extracted from a speech sample with second features extracted from one or more reference samples and to provide a measure of any differences between said first and second features for assessment of said user, wherein said reference samples are limited in bandwidth to the bandwidth of said sampled signals.

10. A system for remote assessment of a user comprising:

application software resident on a server and arranged to interact across a network with a user operating a client device to obtain one or more sample signals of the user's speech;

a datastore arranged to store said one or more user speech samples in association with details of the user;

a feature extraction engine arranged to: extract one or more first features from respective speech samples; and extract one or more second features from one or more reference samples, said reference samples comprising a database of speech samples, wherein prior to operation of said feature extraction engine, said reference samples are distorted in a manner similar to any distortion involved in acquiring said sampled signals across said network; and a comparator arranged to compare said first features extracted from a speech sample with second features extracted from said reference samples and to provide a measure of any differences between said first and second features for assessment of said user.

11. A system for remote assessment of a user comprising:

application software resident on a server and arranged to interact across a network with a user operating a client device to obtain one or more sample signals of the user's speech;

a datastore arranged to store said one or more user speech samples in association with details of the user;

a feature extraction engine arranged to: extract one or more first features from respective speech samples; extract one or more second features from one or more reference samples, said reference samples comprising a database of speech samples, each sample having a pathology associated therewith; and store said second features in association with respective pathologies; and a comparator arranged to: aggregate second features for reference samples associated with like pathologies; compare said first features extracted from a speech sample with second features extracted from said reference samples; and provide respective measures of the difference between said first features and respective aggregated second features for use in assessment of said user.

12. A system as claimed in claim 11 wherein said measures are stored in a datastore in association with user details and wherein said application software is arranged to interact with a clinician to provide respective measures for a speech sample in relation to any pathology having an associated reference sample.

13. A system for remote assessment of a user comprising:

application software resident on a server and arranged to interact across a network with a user operating a client device to obtain one or more sample signals of the user's speech;

a datastore arranged to store said one or more user speech samples in association with details of the user;

a feature extraction engine arranged to extract one or more first features from respective speech samp1es; and a comparator arranged to compare said first features extracted from a speech sample with second features extracted from one or more reference samples and to provide a measure of any differences between said first and second features for assessment of said user, wherein said one or more reference samples comprise a sample signal for said user, and wherein said sample signal is associated with a user state, said user state comprising one of: forced respiration; spontaneous respiration; resting; or after bronchodilator inhalation.

14. A system as claimed in claim 13 wherein said sample signals are between 20 and 120 seconds in duration.

15. A system as claimed in claim 13 wherein sample signals comprise at least one user respiratory cycle.

16. A system as claimed in claim 15 wherein said feature extraction engine is arranged to divide said sample signals into a sequence of one or more inspiration and expiration phases and wherein said first and second features comprise one of a mean or a peak valued frequency component of an expiration phase of a respiratory cycle.

17. A system as claimed in claim 16 wherein said frequency component is calculated based on a temporal subinterval of said expiration phase.

18. A system as claimed in claim 13 wherein said sample signals and said reference samples are band limited between 100 and 2000 Hz.

19. A method operable in a server of remotely assessing a user comprising the steps of:

interacting with a user operating a client device connected to the server across a network to obtain one or more sample signals of the user's speech;

storing said one or more user speech samples in association with details of the user;

extracting one or more first features from respective speech samples;

extracting one or more second features from one or more reference samples, said reference samples comprising a database of speech samples, each sample having a pathology associated therewith, said pathologies comprising: normal, neuromuscular pathologic, physical pathologic and mixed pathologic;

storing said second features in association with respective pathologies; and comparing said first features extracted from a speech sample with second features extracted from said reference samples; and providing a measure of any differences between said first and second features for assessment of said user.

20. A computer program product comprising a computer readable medium comprising computer code which when executed on a server device is arranged to perform the steps of claim 19.

* * * * *